US008227409B2

(12) United States Patent
Kraft et al.

(10) Patent No.: US 8,227,409 B2
(45) Date of Patent: Jul. 24, 2012

(54) DIKETOPIPERAZINE MICROPARTICLES WITH DEFINED ISOMER CONTENTS

(75) Inventors: Kelly S. Kraft, Poughquag, NY (US); Karla Somerville, Corona, CA (US)

(73) Assignee: MannKind Corporation, Valencia, CA (US)

( * ) Notice: Subject to any disclaimer, the term of this patent is extended or adjusted under 35 U.S.C. 154(b) by 270 days.

(21) Appl. No.: 12/813,839

(22) Filed: Jun. 11, 2010

(65) Prior Publication Data

US 2010/0317574 A1 Dec. 16, 2010

Related U.S. Application Data

(60) Provisional application No. 61/186,779, filed on Jun. 12, 2009.

(51) Int. Cl.
*A61K 47/22* (2006.01)
*A61K 38/02* (2006.01)
*A61K 38/22* (2006.01)
*A61K 38/28* (2006.01)
*A61K 38/29* (2006.01)
*A61K 38/26* (2006.01)
*A61K 38/23* (2006.01)
*C07D 241/08* (2006.01)
*A61P 3/10* (2006.01)

(52) U.S. Cl. ........ 514/5.9; 514/1.1; 514/11.7; 514/11.8; 514/11.9; 514/6.9; 514/7.2; 514/784; 514/9.7; 544/385

(58) Field of Classification Search .................. None
See application file for complete search history.

(56) References Cited

U.S. PATENT DOCUMENTS

| 5,352,461 | A | 10/1994 | Feldstein et al. |
| 5,503,852 | A | 4/1996 | Steiner et al. |
| 5,506,203 | A | 4/1996 | Backstrom et al. |
| 5,547,929 | A | 8/1996 | Anderson, Jr. et al. |
| 5,888,477 | A | 3/1999 | Gonda et al. |
| 5,976,569 | A | 11/1999 | Milstein |
| 6,071,497 | A | 6/2000 | Steiner et al. |
| 6,331,318 | B1 | 12/2001 | Milstein |
| 6,395,774 | B1 | 5/2002 | Milstein |
| 6,428,771 | B1 | 8/2002 | Steiner et al. |
| 6,444,226 | B1 | 9/2002 | Steiner et al. |
| 6,635,283 | B2 | 10/2003 | Edwards et al. |
| 6,652,885 | B2 | 11/2003 | Steiner et al. |
| 6,923,175 | B2 | 8/2005 | Poole et al. |
| 7,625,865 | B2 | 12/2009 | Colombo et al. |
| 2004/0182387 | A1 | 9/2004 | Steiner et al. |
| 2006/0040953 | A1 | 2/2006 | Leone-Bay et al. |
| 2007/0196503 | A1 | 8/2007 | Wilson et al. |
| 2009/0308392 | A1* | 12/2009 | Smutney et al. ......... 128/203.15 |

FOREIGN PATENT DOCUMENTS

| EP | 0220958 | 5/1987 |
| WO | 93/18754 A1 | 9/1993 |
| WO | 96/36314 | 11/1996 |
| WO | 99/52506 | 10/1999 |
| WO | 2006/023943 A1 | 3/2006 |
| WO | 2006086107 A2 | 8/2006 |
| WO | 2006105501 A2 | 10/2006 |
| WO | 2007/033316 A2 | 3/2007 |
| WO | 2007098500 A2 | 8/2007 |
| WO | 2007/121411 A2 | 10/2007 |

OTHER PUBLICATIONS

Katchalski, Ephraim, "Synthesis of Lysine Anhydride", J. Amer. Chem. Soc., vol. 68, 1988, pp. 1231-1239.
Kopple, Kenneth D., "A Convenient Synthesis of 2.,5-Piperazinediones", J. Org. Chem., vol. 33, No. 2, 1968, pp. 862-864.
Pfutzner et al. "Pulmonary Insulin Delivery by Means of the Technosphere Drug Carrier Mechanism." Expert Opin Drug Deliv 2:1097-1106, 2005.
Pfutzner et al. "Inhaled Technosphere/Insulin Shows a Low Variability in Metabolic Action in Type 2 Diabetic Patients." Diabetes 49 Supplement, May 2000, A121.
Polonsky et al. "Abnormal Patterns of Insulin Secretion in Non-insulin-Dependent Diabetes Mellitus." N Eng J Med 318:1231-39, 1988.
Raskin et al. "Continuous Subcutaneous Insulin Infusion and Multiple Daily Injection Therapy are Equally Effective in Type 2 Diabetes."Diabetes Care 26:2598-2603, 2003.
Rave et al. "Results of a Dose-Response Study with a New Pulmonary Insulin Formulation and Inhaler." Diabetes 49, Supplement, May 2000, A75.
Rave et al. "Dose Response of Inhaled Dry-Powder Insulin and Dose Equivalence to Subcutaneous Insulin Lispro." Diabetes Care 28:2400-2405, 2005.
Raz et al. "Pharmacodynamics and Pharmacokinetics of Dose Ranging Effects of Oralin Versis S.S. Regular Insulin in Type 1 Diabetic Subjects." Fourth Annual Diabetes Technology Meeting, Philadelphia, 2004.
Rhodes et al. "Technosphere: Microspherical Particles from Substituted Diketopiperazines for Use in Oral Drug Delivery." 208th ACS National Meeting, Aug. 1994.
Rosenstock et al. "Inhaled Insulin Improves Glycemic Control when Substituted for or Added to Oral Combination Therapy in Type 2 Diabetes." Ann Intern Med 143:549-558, 2005.
Rousseau et al. "Drug delivery by fumaryl diketopiperazine particles: evidence for passive transport." Presented at the American Diabetes Association 64th Scientific Sessions, Jun. 2004, abstract 484-P.
Sakagami et al. "Respirable microspheres for inhalation: the potential of manipulating pulmonary disposition for improved therapeutic efficacy." Clin Pharmacokinet 44:263-77, 2005.
Skyler JS et al. "Use of inhaled insulin in a basal/bolus insulin regimen in type 1 diabetic subjects." Diabetes Care 28:1630-1635, 2005.
Steiner et al. "Technosphere®, a novel drug delivery system for oral administration of calcitonin." Pharmaceutical Res 11:S299, 1994.
Steiner et al. "A novel glucagon delivery system for the management of hyperinsulinemia." Diabetes 49 Supplement, May 2000, A368.
Steiner et al. "Bioavailability and pharmacokinetic properties of inhaled dry powder Technosphere®/Insulin." Diabetes 49 Supplement, May 2000, A126.

(Continued)

*Primary Examiner* — David J Blanchard
*Assistant Examiner* — Garen Gotfredson
(74) *Attorney, Agent, or Firm* — K&L Gates LLP; Louis C. Cullman; Brent A. Johnson

(57) ABSTRACT

Disclosed herein are fumaryl diketopiperazine (FDKP) compositions and microparticles having a specific trans isomer content of about 45% to about 65%. The FDKP microparticles can comprise a drug such as an endocrine hormone, including, peptide, including, insulin, glucagon, parathyroid hormones and the like and can be used to make a powder formulation for pulmonary delivery of the drug.

30 Claims, 6 Drawing Sheets

OTHER PUBLICATIONS

Steiner et al. Technosphere(TM)/Insulin—proof of concept study with a new insulin formulation for pulmonary delivery. Exp Clin Endocrinol Diabetes 110:17-21, 2002.
Taylor et al. "Aerosols for macromolecule delivery. Design challenges and solutions." Am J Drug Deliv 2:143-155, 2004.
Warren et al. "Postprandial versus prandial dosing of biphasic insulin aspart in elderly type 2 diabetes patients." Diabetes Res Clin Pract 66:23-29, 2004.
White JR et al. "Inhaled insulin: an overview." Clinical Diabetes 19:13-16, 2001.
International Search Report, PCT/US2010/038287.
"An inhaled insulin formulation (Technosphere Insulin) effectively improves glycaemic control in patients with type 2 diabetes mellitus." Inpharma Weekly, vol. 1522, Jan. 28, 2006, p. 8.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bayés M et al. "Gateways to clinical trials" Methods Find Exp Clin Pharmacol 24:431-455, 2002.
Belmin J et al. "Novel drug delivery systems for insulin. Clinical potential for use in the elderly." Drugs Aging 20:303-12, 2003.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Brownlee M et al. "Glycemic variability: a hemoglobin Al c-independent risk factor for diabetic complications." JAMA 295:1707-8, 2006.
Caumo et al. "First-phase insulin secretion: does it exist in real life" Considerations on shape and function. Am J Physiol Endocrinol Metab 287:E371-E385, 2004.
Cefalu "Concept, strategies and feasibility of noninvasive insulin delivery." Diabetes Care 27:239-246, 2004.
Cefalu "Novel routes of insulin delivery for patients with type 1 or type 2 diabetes." Ann Med 33:579-586, 2001.
Cerasi et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cheatham et al. "Desirable dynamics and performance of inhaled insulin compared to subcutaneous insulin given at mealtime in type 2 diabetes: A report from the Technosphere®/Insulin study group." Diabetes Tech Ther 6:234-235, 2004.
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Del Prato "Unlocking the opportunity of tight glycaemic control. Far from goal." Diabetes Obesity Metabolism 7:S1-S4, 2005.
Edelman SV Type II diabetes mellitus. Adv Int Med 43:449-500, 1998.
Gates BJ "Update on advances in alternative insulin therapy." Advances in Pharmacy 1:159-168, 2003.
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Gupta et al. Contemporary approaches in aerosolized drug delivery to the lung. J Controlled Resease 17:129-148, 1991.
Harsch IA "Inhaled Insulins: Their potential in the treatment of diabetes mellitus." Treat Endocrinol 4:131-138, 2005.
Heinemann, L., et al., "Current status of the development of inhaled insulin" Br. Diabetes Vasc Dis 4:295-301, 2004.
Hirsch IB "Insulin analogues." N Engl J Med 352:174-83, 2005.
Kapitza et al. "Dose-response characteristics for a new pulmonary insulin formulation and inhaler." Presented at the 35th Annual Meeting of the EASD, Sep. 2000, abstract OP29 184.
Kohler et al. Non-radioactive approach for measuring lung permeability: inhalation of insulin. Atemw Lungenkrkh 13:230-232, 1987. (Original German and English translation attached).
Krueger et al. "Toxicological profile of pulmonary drug delivery agent." Presented at the American Diabetes Association 64th Scientific Sessions, Jun. 2004, abstract 465-P.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Leiner et al. "The pharmacokinetic profile of insulin administered by inhalation in the rat." Diabetes 53 Supplement, Jun. 2004, A111.
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Lian et al. A self-complementary self-assembling microsphere system: application for intravenous delivery of the antiepileptic andneuroprotectant compound felbanate. J Pharm Sci 89:867-875, 2000.
Lindner et al. "Increase in serum insulin levels is correlated with lung distribution after pulmonary delivery of Technosphere/Insulin." Diabetologia 46:A277, 2003.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
Monnier et al. "Activation of oxidative stress by acute glucose fluctuations compared with sustained chronic hyperglycemia in patients with type 2 diabetes." JAMA 295:1681-7, 2006.
Nathan et al. "Intensive diabetes treatment and cardiovascular disease in patients with type 1 diabetes." N Engl J Med 353:2643-53, 2005.
Owens et al. "Alternative routes of insulin delivery." Diabetic Medicine 20:886-898, 2003.
Patton et al. "Clinical pharmacokinetics and pharmacodynamics of inhaled insulin." Clin Pharmacokinet 43:781-801, 2004.
Peyrot et al. "Resistance to insulin therapy among patients and providers." Diabetes Care 28:2673-2679, 2005.
Pfeiffer et al. Insulin secretion in diabetes mellitus. Am J Med 70:579-88, 1981.
Pfützner A. et al. "Influence of small dose i.v., s.c. and pulmonary insulin treatment on prandial glucose control in patients with Type 2 diabetes." 37th Annual Meeting of the EASD, Sep. 9-13, 2001, abstract 812.
Pfützner A et al. "Technosphere®/Insulin—a new approach for effective delivery of human insulin via the pulmonary route." Diab Tech Ther 4:589-594, 2002.

Pfützner A et al. "Variability of insulin absorption after subcutaneous and pulmonary application in patients with type 2 diabetes." Diabetes 51 Supplement, Jun. 2002, A47-48.

Pfützner A et al. Pilot study with Technosphere/PTH(1-34)—a new approach for effective pulmonary delivery of parathyroid hormone (1-34). Horm Metab Res 35:319-323, 2003.

Pfützner A et al. "Lung distribution of radiolabeled Technosphere™/Insulin." Diabetes 52 Supplement, Jun. 2003, A107.

CN Office Action cited in Application No. 200880122670.3 mailed on Nov. 23, 2011.

* cited by examiner

DIKETOPIPERAZINE MICROPARTICLES WITH DEFINED ISOMER CONTENTS

CROSS REFERENCE TO RELATED APPLICATIONS

This application claims benefit under 35 U.S.C. §119(e) from U.S. Provisional Patent Application Ser. No. 61/186,779, filed Jun. 12, 2009, the content of which is incorporated herein by reference in its entirety.

TECHNICAL FIELD

Disclosed herein are fumaryl diketopiperazine (FDKP) compositions and microparticles having a specific trans isomer content of about 45% to about 65%. The FDKP microparticles can be used as a delivery system for drugs or active agents in the treatment of disease or disorders, for example, those of endocrine origin, including diabetes and obesity.

BACKGROUND

Delivery of drugs has been a major problem for many years, particularly when the compound to be delivered is unstable under the conditions encountered in the gastro-intestinal tract when administered orally to a subject, prior to reaching its targeted location. For example, it is preferable in many cases to administer drugs orally, especially in terms of ease of administration, patient compliance, and decreased cost. However, many compounds are ineffective or exhibit low or variable potency when administered orally. Presumably this is because the drugs are unstable to conditions in the digestive tract or because they are inefficiently absorbed.

Due to the problems associated with oral drug delivery, drug delivery to the lungs has been explored. For example, typically drugs delivered to the lungs are designed to have an effect on the tissue of the lungs, for example, vasodilators, surfactants, chemotherapeutic agents or vaccines for flu or other respiratory illnesses. Other drugs, including nucleotide drugs, have been delivered to the lungs because they represent a tissue particularly appropriate for treatment, for example, for genetic therapy in cystic fibrosis, where retroviral vectors expressing a defective adenosine deaminase are administered to the lungs.

Drug delivery to the lungs for agents having systemic effects can also be performed. Advantages of the lungs for delivery of systemic agents include the large surface area and the ease of uptake by the lung's mucosal surface. One problem associated with all of these forms of pulmonary drug delivery is that it is difficult to deliver drugs into the lungs due to problems in getting the drugs past all of the natural barriers, such as the cilia lining the trachea, and in trying to administer a uniform volume and weight of drug.

Accordingly, there is room for improvement in the pulmonary delivery of drugs.

SUMMARY

The present disclosure provides systems, microparticles and methods that allow for improved delivery of drugs to the lungs. Embodiments disclosed herein achieve improved delivery by providing diketopiperazine microparticles comprising a defined isomer content. In particular, the diketopiperazine microparticles are exemplified by fumaryl diketopiperazine (FDKP) compound having a trans isomer content of about 45% to about 65%. FDKP microparticles having a trans isomer content in this range exhibit characteristics beneficial to drug delivery to the lungs such as improved aerodynamic performance.

One embodiment disclosed herein comprises FDKP microparticles comprising a trans isomer content of about 45% to about 65%. In other embodiments of the FDKP microparticles, the trans isomer content can be from about 50% to about 65%, from about 52% to 62%, or from about 53% to about 65%. In another embodiment of the FDKP microparticles, the trans isomer content is from about 53% to about 63%.

In another embodiment, the FDKP microparticles comprise a drug or active agent. In various embodiments of the FDKP microparticles, the drug can be, for example, a peptide, including, insulin, glucagon-like peptide-1 (GLP-1), glucagon, exendin, parathyroid hormone, calcitonin, oxyntomodulin, and the like. In another embodiment of the FDKP microparticles, the peptide content can vary depending on downstream processing conditions. In a particular example, the FDKP microparticles can be prepared to have drug/peptide content that can vary depending on the dose to be targeted or delivered. For example, wherein the drug is insulin, the insulin component can be from about 3 U/mg to about 4 U/mg in the powder formulation comprising the microparticles. In certain embodiments the drug is adsorbed to the surfaces of the microparticles.

Embodiments disclosed herein also include dry powders comprising the microparticles. In one embodiment, the dry powders comprise FDKP microparticles comprising a trans isomer content of about 45% to about 65%. In other embodiments of the dry powders, the FDKP microparticles can have a trans isomer content from about 50% to about 65%, from about 52% to 62%, or from about 53% to about 65%. In another embodiment of the dry powders comprising the FDKP microparticles, the trans isomer content is from about 53% to about 63%.

In another embodiment of the dry powders, the FDKP microparticles comprise a drug. In another embodiment of the dry powders, the drug is a peptide of various molecular size or mass, including; insulin, glucagon-like peptide-1, glucagon, exendin, parathyroid hormone, calcitonin, oxyntomodulin, and the like. In one embodiment of the dry powders, wherein the trans isomer content of fumaryl diketopiperazine ranges between 45% and 65% and the drug is insulin, the insulin content of the FDKP microparticles is from about 3 U/mg to about 4 U/mg.

Further embodiments concern drug delivery systems comprising an inhaler, a unit dose dry powder medicament container, for example, a cartridge, and a powder comprising the microparticles disclosed herein and an active agent. In one embodiment, the delivery system for use with the dry powders includes an inhalation system comprising a high resistance inhaler having air conduits which impart a high resistance to airflow through the conduits for deagglomerating and dispensing the powder. In one embodiment, the inhalation system has a resistance value of, for example, approximately 0.065 to about 0.200 ($\sqrt{kPa}$)/liter per minute. In certain embodiments, the dry powders can be delivered effectively by inhalation with an inhalation system wherein the peak inhalation pressure differential can range from about 2 to about 20 kPa, which can produce resultant peak flow rates of about between 7 and 70 liters per minute. In certain embodiments, the inhalation system are configured to provide a single dose by discharging powder from the inhaler as a continuous flow, or as one or more pulses of powder delivered to a patient. In some embodiments disclosed herewith, the dry powder inhaler system comprises a predetermined mass flow balance within the inhaler. For example, a flow balance of approximately 10% to 70% of the total flow exiting the inhaler and into the patient is delivered by one or more dispensing ports, which airflow passes through the area containing the powder formulation, and wherein approximately 30% to 90% air flow is generated from other conduits of the inhaler. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the mouthpiece. In one embodiment, flow rates ranging from about 7 to 70 liters per minute result in greater than 75% of the container or the cartridge contents dispensed in fill masses between 1 and 30 mg. In certain embodiments, an inhalation system as described above can emit a respirable fraction/fill of a powder dose at percentages greater than 40% in a single inhalation, greater than 50%, greater than 60%, or greater than 70%.

In particular embodiments, an inhalation system is provided comprising a dry powder inhaler, a dry powder formulation comprising microparticles of fumaryl diketopiperazine having an FDKP trans isomer content between 45% and 65% and one or more than one active agents. In some aspects of this embodiment of the inhalation system, the dry powder formulation is provided in a unit dose cartridge. Alternatively, the dry powder formulation can be preloaded in the inhaler. In this embodiment, the structural configuration of the inhalation system allows the deagglomeration mechanism of the inhaler to produce respirable fractions greater than 50%; that is, more than half of the powder contained in the inhaler (cartridge) is emitted as particles of less than 5.8 µm. The inhalers can discharge greater than 85% of a powder medicament contained within a container during dosing. In certain embodiments, the inhalers can discharge greater than 85% of a powder medicament contained in a single inhalation. In one embodiment, the inhalers can discharge greater that 90% of the cartridge contents or container contents in less than 3 seconds at pressure differentials between 2 and 5 kPa with fill masses ranging up to 30 mg.

Embodiments disclosed herein also include methods. In one embodiment, a method of treating an endocrine-related disease or disorder comprising administering to a person in need thereof a dry powder formulation comprising FDKP microparticles comprising an FDKP trans isomer content of about 45 to about 65% and a drug suitable to treat said disease or disorder. One embodiment includes a method of treating an insulin-related disorder comprising administering a dry powder comprising microparticles of FDKP described above to a person in need thereof. The method comprises administering to a subject a dry powder formulation comprising microparticles of fumaryl diketopiperazine having a trans isomer content ranging from about 45% to 65% or from about 45% to about 63%. In various embodiments an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder. In one embodiment, the dry powder comprises insulin. In other embodiments, the dry powder comprises glucagon, an exendin, or GLP-1.

Another embodiment disclosed herein includes a method of making microparticles suitable for pulmonary administration as a dry powder comprising: a) synthesizing an FDKP compound having a trans isomer content from about 45% to about 65%; b) determining the trans isomer content of the FDKP compound to assess that the trans isomer content range is from about 45% to about 65%; c) dissolving the FDKP compound of step b) in a solution having a basic pH to form an FDKP solution; d) providing a solution of a volatile acid, and e) mixing the FDKP solution with the solution of a volatile acid together in a high-shear mixer to produce the microparticles. In one embodiment, the step of determining the trans isomer content of the FDKP compound is performed using high pressure liquid chromatography (HPLC). In alternative embodiments, isomer content is determined subsequent to particle formation.

In another embodiment, a method for synthesizing a diketopiperazine having a trans isomer content of about 45% to about 65% is disclosed, the method comprising: providing a diketopiperazine having an ester group; saponifying the ester group of the diketopiperazine in a mixture of water and a water-miscible solvent at a basic pH; and recrystallizing the diketopiperazine in a reaction mixture comprising trifluoroacetic acid and glacial acid at a resultant ratio ranging from about 0.4 to about 0.7, respectively. In this and other embodiments, the reaction mixture in the recrystallizing step is held or allowed to continue for a period of about 4 hours or greater than 4 hours.

In one embodiment of the method of synthesis, the water-miscible solvent is an alcohol, including, methanol, ethanol, or isopropanol. Other solvents such as tetrahydrofuran, dioxane, acetone, and acetonitrile can also be used. In this and other embodiments, the method further comprises the step of determining the trans isomer content of the diketopiperazine.

In a specific embodiment, the method of making a diketopiperazine having a trans isomer content of about 45% to about 65%, utilizes a diketopiperazine having the formula 2,5-diketo-3,6-bis(N—X-4-aminobutyl)piperazine, wherein X is selected from the group consisting of fumaryl, succinyl, maleyl, and glutaryl. In an exemplary embodiment, the diketopiperazine has the formula 2,5-diketo-3,6-bis(N-fumaryl-4-aminobutyl)piperazine.

In particular embodiments, the method for making a DKP compound having a DKP trans isomer content ranging from about 45% to about 65% comprises a saponification reaction and a recrystallization reaction. In one embodiment, the method comprises a saponification reaction of a diketopiperazine compound comprising an ester protecting group, including, an alkyl ester such as ethyl ester, or methyl ester. In one embodiment, the step of synthesizing an FDKP compound having a trans isomer content from about 45% to about 65% comprises saponifying an ester of an FDKP in a solvent such as a water-based solvent and adding a base. In a particular embodiment, the method comprises dissolving the DKP such as fumaryldiketopiperazine ethyl ester in a solvent such as water:methanol at a ratio of 1:1 to about 3:1, respectively. In other embodiments, other water-miscible solvents can be used, including, other alcohols, tetrahydrofuran, dioxane, acetone, acetonitrile and the like. In one embodiment, the solvent can comprise water only. In this and other embodiments, the saponification reaction further comprises adding a solution comprising sodium hydroxide; holding the reaction mixture at a temperature ranging from about 20° C. to about 60° C. or to refluxing conditions; filtering the reaction mixture to yield a filtrate; adding an acidic solution to the filtrate, and collecting the solid material formed by filtration and washing the FDKP solid material. The solid material can then be analyzed to determine the trans isomer content of the FDKP particles formed.

In a particular embodiment, the method comprises recrystallizing the FDKP material comprising heating a suspension of FDKP in trifluoroacetic acid to about 40° C. to about 85° C. for about 1 minute to about 2 hours and cooling the reaction; adding glacial acetic acid to the solution and cooling the suspension for about 1 to about 24 hours at about 20° C. In one embodiment, the crystallization step comprises conducting the reaction at a crystallization temperature ranging from about 15° C. to about 25° C., for about 1 hour to about 6.5 hours in a solution comprising trifluoroacetic acid:glacial acetic acid, respectively, in a ratio ranging from about 0.4 to about 0.7. In this embodiment, the method further comprises washing the reaction mixture with glacial acetic and cooling the temperature of the reaction at a rate of from about 7° C. to about 10° C. per hour. Other cooling rates may be used to obtain an FDKP material having desired isomer contents.

Another embodiment disclosed herein includes a method of delivering insulin to a patient in need thereof comprising administering a dry powder comprising diketopiperazine microparticles disclosed herein to the deep lung by inhalation of the dry powder by the patient. In aspects of this embodiment, particular features of an inhaler system are specified.

BRIEF DESCRIPTION OF THE DRAWINGS

The following drawings form part of the present specification and are included to further demonstrate certain aspects of the examples disclosed herein. The disclosure may be better understood by reference to one or more of these drawings in combination with the detailed description of specific embodiments presented herein.

DETAILED DESCRIPTION

Figure 1:
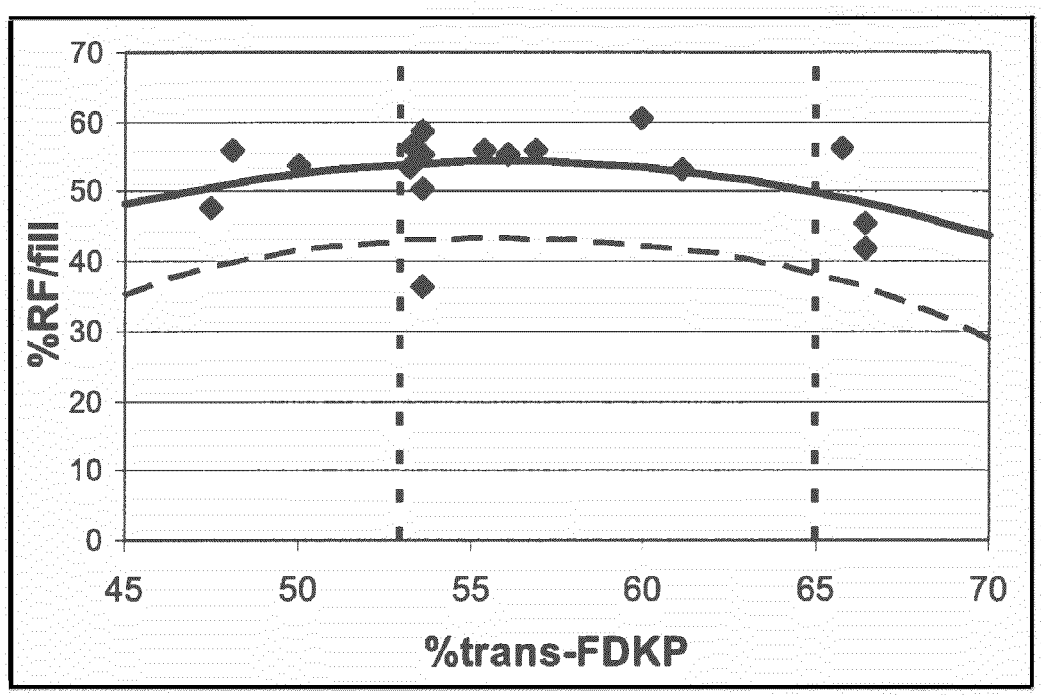
FIG. 1 depicts aerodynamic powder performance as a function of % trans isomer content.
Figure 2:
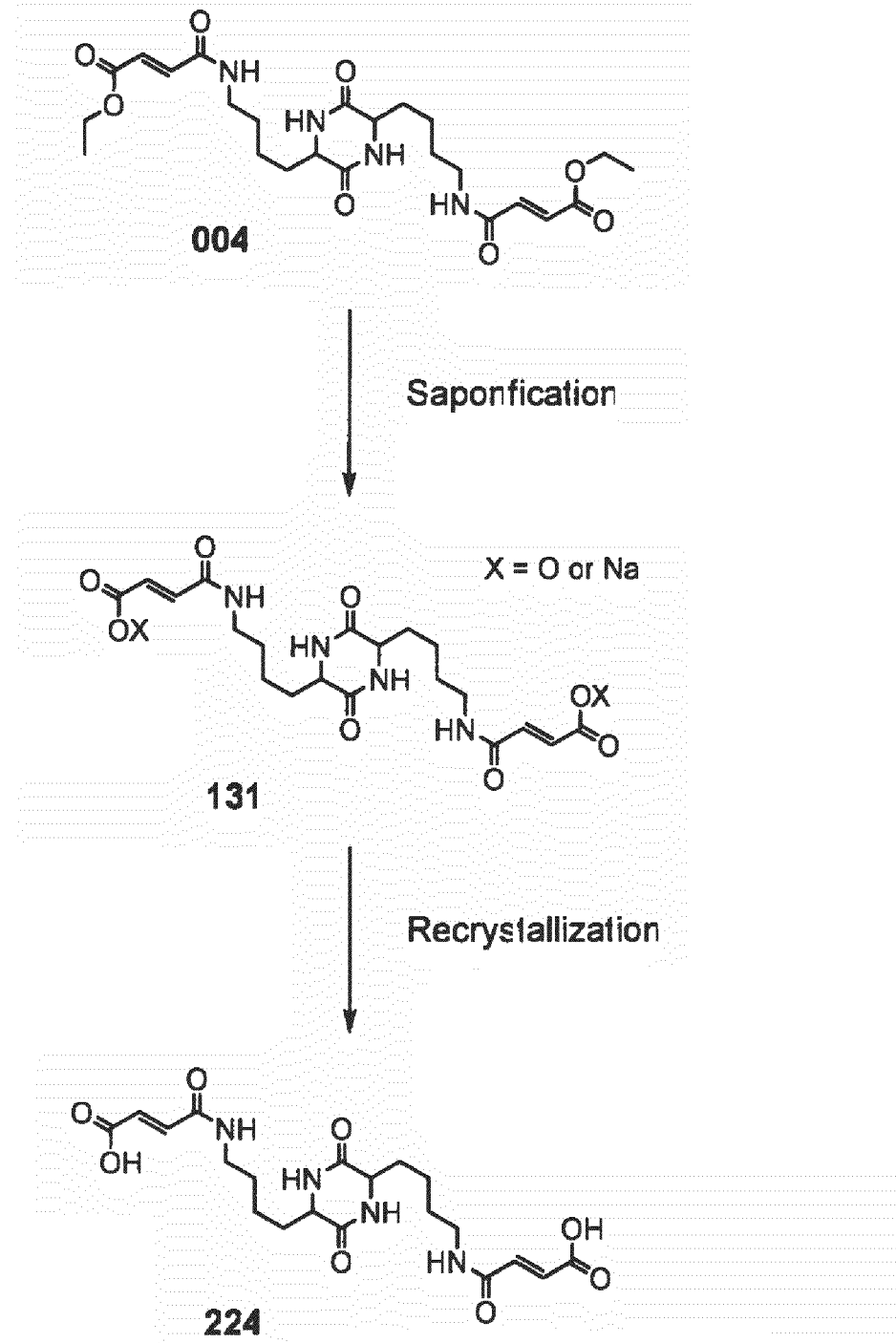
FIG. 2 depicts steps in a synthetic scheme that can be controlled so as to produce FDKP with a trans isomer content of about 45 to about 65%.
Figure 3:
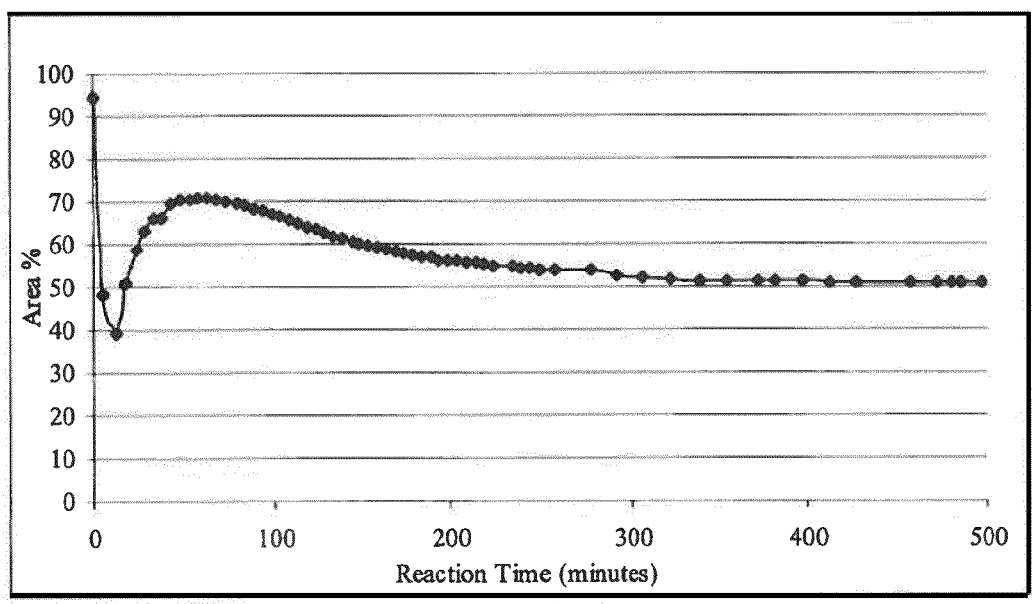
FIG. 3 depicts % trans isomer content as a function of slow NaOH addition during the saponification step of the scheme depicted in FIG. 2.
Figure 4:
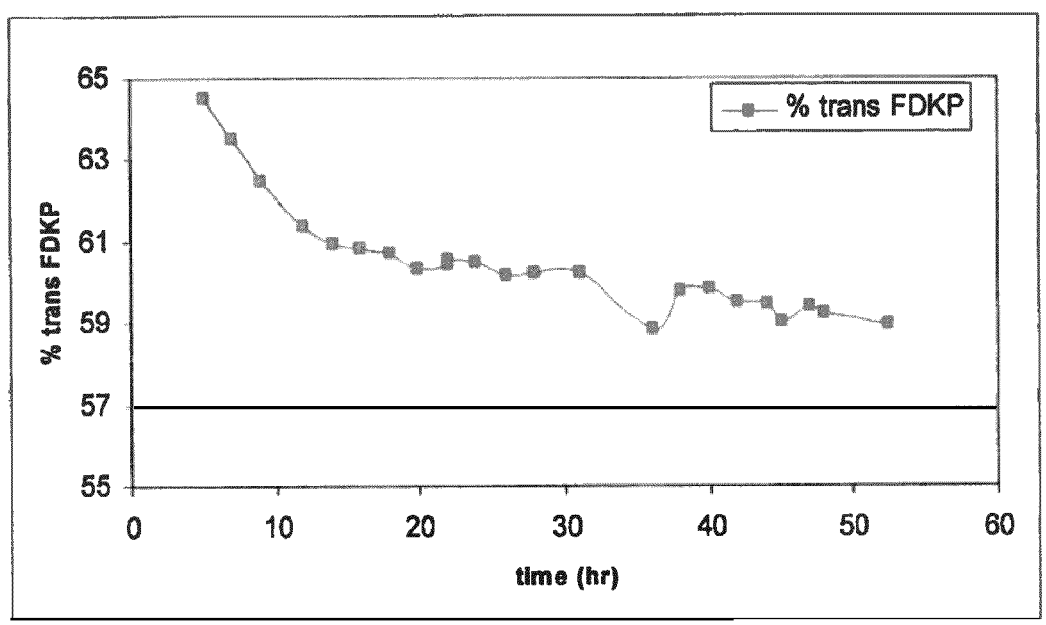
FIG. 4 depicts % trans isomer content after trifluoroacetic acid (TFA) recrystallization using a fast cooling ramp.

As stated, drug delivery to the lungs offers many advantages. It is difficult to deliver drugs into the lungs, however, due to problems in transporting the drugs past natural physical barriers in a uniform volume and weight of the drug. Disclosed herein are diketopiperazines having a defined trans isomer content, microparticles as drug delivery agents, methods of making the microparticles and methods of treatment using the microparticles.

As used herein, the term "microparticle" refers to a particle with a diameter of about 0.5 to about 1000 μm, irrespective of the precise exterior or interior structure. Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. To reach the deep lung (or alveolar region) where most efficient absorption is believed to occur, it is preferred to maximize the proportion of particles contained in the "respirable fraction" (RF), generally accepted to be those particles with an aerodynamic diameter of about 0.5 to about 5.7 microns, though some references use somewhat different ranges, as measured using standard techniques, for example, with an Anderson Cascade Impactor. Other impactors can be used to measure aerodynamic particle size such as the NEXT GENERATION IMPACTOR™ (NGI™, MSP Corporation), for which the respirable fraction is defined by similar aerodynamic size, for example <6.4 μm. In some embodiments, a laser diffraction apparatus is used to determine particle size, for example, the laser diffraction apparatus disclosed in U.S. patent application Ser. No. 12/727,179, filed on Mar. 18, 2010, which is incorporated herein in its entirety for its relevant teachings, wherein the volumetric median geometric diameter (VMGD) of the particles is measured to assess performance of the inhalation system. For example, in various embodiments cartridge emptying of ≧80%, 85%, or 90% and a VMGD of the emitted particles of ≦12.5 μm, ≦7.0 μm, or ≦4.8 μm can indicate progressively better aerodynamic performance. Embodiments disclosed herein show that FDKP microparticles with a trans isomer content of between about 45% to about 65% exhibit characteristics beneficial to delivery of drugs to the lungs such as improved aerodynamic performance.

Respirable fraction on fill (RF/fill) represents the % of powder in a dose that is emitted from an inhaler upon discharge of the powder content filled for use as the dose, and that is suitable for respiration, i.e., the percent of particles from the filled dose that are emitted with sizes suitable for pulmonary delivery, which is a measure of microparticle aerodynamic performance. As described herein, a RF/fill value of 40% or greater than 40% reflects acceptable aerodynamic performance characteristics. In certain embodiments disclosed herein, the respirable fraction on fill can be greater than 50%. In an exemplary embodiment, a respirable fraction on fill can be up to about 80%, wherein about 80% of the fill is emitted with particle sizes <5.8 μm as measured using standard techniques.

As used herein, the term "dry powder" refers to a fine particulate composition that is not suspended or dissolved in a propellant, carrier, or other liquid. It is not meant to necessarily imply a complete absence of all water molecules.

It should be understood that specific RF/fill values can depend on the inhaler used to deliver the powder. Powders generally tend to agglomerate and crystalline DKP microparticles form particularly cohesive powders. One of the functions of a dry powder inhaler is to deagglomerate the powder so that the resultant particles comprise a respirable fraction suitable for delivering a dose by inhalation. However, deagglomeration of cohesive powders is typically incomplete so that the particle size distribution seen when measuring the respirable fraction as delivered by an inhaler will not match the size distribution of the primary particles, that is, the profile will be shifted toward larger particles. Inhaler designs vary in their efficiency of deagglomeration and thus the absolute value of RF/fill observed using different designs will also vary. However, optimal RF/fill as a function of isomeric content will be similar from inhaler to inhaler.

As used herein, the term "about" is used to indicate that a value includes the standard deviation of the measurement for the device or method being employed to determine the value.

Diketopiperazines

One class of drug delivery agents that has been used to overcome problems in the pharmaceutical arts such as drug instability and/or poor absorption are the 2,5-diketopiperazines. 2,5-Diketopiperazines are represented by the compound of the general Formula 1 as shown below wherein $E_1$ and $E_2$ are independently N or more particularly NH. In other embodiments, $E_1$ and/or $E_2$ are independently an oxygen or a nitrogen so that wherein either one of the substituents for $E_1$ and $E_2$ is an oxygen and the other is a nitrogen the formula yields the substitution analog diketomorpholine, or when both $E_1$ and $E_2$ are oxygen the formula yields the substitution analog diketodioxane.

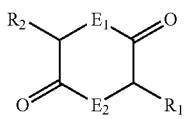

Formula 1

These 2,5 diketopiperazines have been shown to be useful in drug delivery, particularly those bearing acidic $R_1$ and $R_2$ groups as described in, for example, U.S. Pat. Nos. 5,352,461 entitled "Self Assembling Diketopiperazine Drug Delivery System;" 5,503,852 entitled "Method For Making Self-Assembling Diketopiperazine Drug Delivery System;" 6,071,497 entitled "Microparticles For Lung Delivery Comprising Diketopiperazine;" and 6,331,318 entitled "Carbon-Substituted Diketopiperazine Delivery System," each of which is incorporated herein by reference in its entirety for all that it teaches regarding diketopiperazines and diketopiperazine-mediated drug delivery. Diketopiperazines can be formed into microparticles that incorporate a drug or microparticles onto which a drug can be adsorbed. The combination of a drug and a diketopiperazine can impart improved drug stability and/or absorption characteristics. These microparticles can be administered by various routes of administration. As dry powders these microparticles can be delivered by inhalation to specific areas of the respiratory system, including the lungs.

Such microparticles are typically obtained by pH-based precipitation of the free acid (or base) resulting in self-assembled microparticles comprised of aggregated crystalline plates. The stability of the particle can be enhanced by small amounts of a surfactant, such as polysorbate-80, in the DKP solution from which the particles are precipitated (see for example US Patent Publication No. 2007/0059373 entitled "Method of drug formulation based on increasing the affinity of crystalline microparticle surfaces for active agents" which is incorporated herein by reference in its entirety for all that it teaches regarding the formation and loading of DKP microparticles and dry powders thereof). Ultimately solvent can be removed to obtain a dry powder. Appropriate methods of solvent removal include lyophilization and spray drying (see for example US Patent Publication No. 2007/0196503 entitled "A method for improving the pharmaceutic properties of microparticles comprising diketopiperazine and an active agent" and U.S. Pat. No. 6,444,226 entitled "Purification and stabilization of peptide and protein pharmaceutical agents" each of which is incorporated herein by reference in its entirety for all that it teaches regarding the formation and loading of DKP microparticles and dry powders thereof). The microparticles disclosed herein are distinct from microparticles composed of DKP salts. Such particles are typically formed (as opposed to dried) by spray drying, resulting in spheres and/or collapsed spheres of an amorphous salt (as opposed to a free acid or base) so that they are chemically, physically, and morphologically distinct entities. The present disclosure refers to FDKP to be understood as the free acid or the dissolved anion.

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference in their entirety. 2,5-Diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with an appropriate reagent and conditions. For example, CBz-protecting groups can be removed using 4.3 M HBr in acetic acid. This route can be preferred because it uses a commercially available starting material, it involves reaction conditions that are reported to preserve stereochemistry of the starting materials in the product and all steps can be easily scaled up for manufacture. Methods for synthesizing diketopiperazines are also described in U.S. Pat. No. 7,709,639, entitled, "Catalysis of Diketopiperazine Synthesis," which is also incorporated by reference herein for its teachings regarding the same.

Fumaryl diketopiperazine (2,5-diketo-3,6-bis(N-fumaryl-4-aminobutyl)piperazine; FDKP) is one preferred diketopiperazine for pulmonary applications:

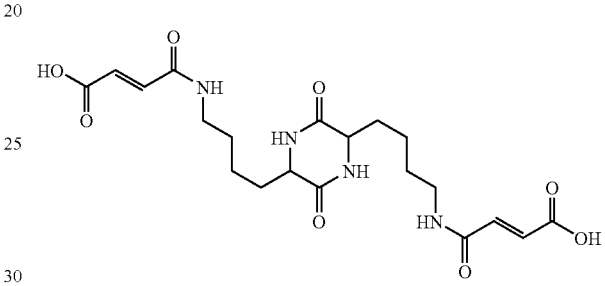

FDKP provides a beneficial microparticle matrix because it has low solubility in acid but is readily soluble at neutral or basic pH. These properties allow FDKP to crystallize and the crystals to self-assemble into form microparticles under acidic conditions. The particles dissolve readily under physiological conditions where the pH is neutral. As noted, microparticles having a diameter of between about 0.5 and about 10 microns can reach the lungs, successfully passing most of the natural barriers. Particles in this size range can be readily prepared from FDKP.

FDKP possesses two asymmetric centers in the diketopiperazine ring. FDKP is manufactured as a mixture of geometric isomers that are identified as "cis-FDKP" and "trans-FDKP" according to the arrangement of side chains relative to the central "ring" of the diketopiperazine. The R,R and S,S enantiomers have the propenyl(amidobutyl) "side arms" projecting from the same planar side of the diketopiperazine ring (A and B below) and are thus referred to as the cis isomers while the R,S compound has the "side arms" projecting from opposite planar sides of the diketopiperazine ring (C below) and is referred to as the trans isomer.

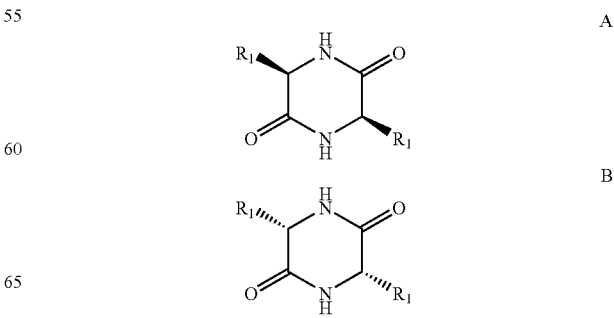

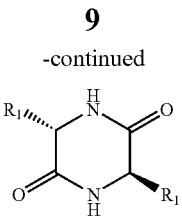

-continued

C

FDKP microparticle powders with acceptable aerodynamic performance, as measured by RF/fill with moderately efficient inhalers such as the MEDTONE® inhaler disclosed in U.S. Pat. No. 7,464,706 entitled, "Unit Dose Cartridge and Dry Powder Inhaler," which is incorporated by reference herein for its teachings regarding the same, have been produced from FDKP with a trans isomer content ranging from about 45 to about 65%. Particles with isomer content in this range also perform well with high efficiency inhalers such as those disclosed in U.S. patent application Ser. No. 12/484,125 entitled, "A Dry Powder Inhaler and System for Drug Delivery," filed on Jun. 12, 2009, and U.S. patent application Ser. No. 12/717,884, entitled, "Improved Dry Powder Drug Delivery System," filed on Mar. 4, 2010, which disclosures are herein incorporated by reference for its teachings regarding the same. Powders comprising microparticles containing more than 65% trans-FDKP tend to have lower and more variable RF/fill (FIG. 1). Trans isomer-enriched microparticles of FDKP have altered morphology and also lead to viscous suspensions which are difficult to process.

In other experiments done under comparable conditions to those reported in FIG. 1, microparticles made from about 95% trans-enriched FDKP and insulin produced an RF/fill of about 24%, whereas control samples with a trans isomer content of about 59% with equal insulin content gave an RF/fill of about 49-52% (data not shown). Accordingly, an FDKP microparticle powder having a trans isomer content of about 45% to about 65% provides a powder with acceptable aerodynamic properties. In alternate embodiments the FDKP trans isomer content ranges from about 50% to about 65% from about 52% to about 62% or from about 53% to about 63% (see FIG. 1).

Based on the foregoing, it is desirable to produce microparticle powders having a trans isomer content within the range of about 45% to about 65%. Thus, the present disclosure ascertains that trans isomer content would affect the aerodynamic performance of FDKP microparticles, which was not anticipated. However, it was discovered that improved consistency could be obtained by carefully controlling the isomer content of the FDKP used to make FDKP microparticles. In FIG. 1, the solid curved line represents predicted RF/fill and the dashed curved line represents the one-sided lower 95% confidence limit of obtaining a suitable RF/fill score. The vertical dashed lines provide limits on the trans isomer content for one exemplary embodiment disclosed herein.

The FDKP cis/trans isomer ratio is established during the manufacturing steps depicted in FIG. 2. FIG. 2 depicts steps in a synthetic scheme that can be controlled so as to produce FDKP with a trans isomer content of about 45% to about 65%. In the synthetic scheme, there are several parameters and/or reaction steps including, saponification and recrystallization, during synthesis of FDKP that can be regulated to obtain the targeted or desired isomer ratio. For example, specific parameters of the reactions, including, temperature, reaction time, and the type of solvents or co-solvents used, can be controlled to yield a product with the desired or targeted trans isomer content.

Control of the Lower End of the Range of FDKP Trans Isomer Content

The lower end of the trans isomer content is controlled by exposing the DKP ring to a strong base. In one manufacturing step, ethyl protecting groups are removed by saponification with sodium hydroxide. These basic conditions also promote ring epimerization between isomers as shown below, without regard for which isomer is in excess. For example, the addition of a base to a reaction comprising a starting compound composed of, for example, 95% trans isomer can yield an FDKP material comprised of approximately 50/50 mixture of cis and trans isomer content (FIG. 3). In addition to basic pH, other factors can also contribute to the regulation of trans isomer content formation, including, concentration of solvents and co-solvents, time of exposure and temperature of the reaction.

trans cis

Control of the Upper End of the Range or FDKP Trans Isomer Content

Differences in solubility between the isomers affect the FDKP isomer content. For instance, FDKP can be recrystallized from trifluoroacetic acid (TFA) and glacial acetic acid (GAA). Trans FDKP is less soluble in this solvent system than cis FDKP. Accordingly, conditions that favor selective precipitation of the less soluble trans isomer can be used to increase the trans isomer content of the final product. Such conditions include decreased recrystallization time, anti-solvent addition at low temperature and/or rapid cooling of the trifluoroacetic acid-glacial acetic acid (TFA-GAA) mixture (FIG. 4). It will also be appreciated that elevating the trans isomer content by such methods provides a residual solution of FDKP enriched in the cis isomers.

TABLE 1

| Exemplary Manufacturing Ranges | |
|---|---|
| Parameter | Operating Range |
| TFA/GAA* Ratio | 0.67 ± 0.05 |
| Crystallization Time (hrs) | 6 ± 0.5 |
| Crystallization Temp (° C.) | 15-25 |
| Cooling Ramp Post GAA Addition (° C./hr) | 7-10 |

*Denotes trifluoroacetic acid:glacial acid acid

Providing microparticles with an isomer content in the about 45% to about 65% range provides microparticles with beneficial aerodynamic characteristics.

Selection and Incorporation of Active Agents

As long as the microparticles described herein retain the required isomer content, they can adopt other additional characteristics beneficial for delivery to the lung and/or drug adsorption. U.S. Pat. No. 6,428,771 entitled "Method for Drug Delivery to the Pulmonary System" describes DKP particle delivery to the lung and is incorporated by reference herein for its teachings regarding the same. U.S. Pat. No. 6,444,226, entitled, "Purification and Stabilization of Peptide and Protein Pharmaceutical Agents" describes beneficial methods for adsorbing drugs onto microparticle surfaces and is also incorporated by reference herein for its teachings regarding the same. Microparticle surface properties can be manipulated to achieve desired characteristics as described in U.S. patent application Ser. No. 11/532,063 entitled "Method of Drug Formulation based on Increasing the Affinity of Crystalline Microparticle Surfaces for Active Agents" which is incorporated by reference herein for its teachings regarding the same. U.S. patent application Ser. No. 11/532,065 entitled "Method of Drug Formation based on Increasing the Affinity of Active Agents for Crystalline Microparticle Surfaces" describes methods for promoting adsorption of active agents onto microparticles. U.S. patent application Ser. No. 11/532,065 is also incorporated by reference herein for its teachings regarding the same.

The microparticles described herein can comprise one or more active agents. As used herein "active agent", used interchangeably with "drug", refers to pharmaceutical substances, including small molecule pharmaceuticals, biologicals and bioactive agents. Active agents can be naturally occurring, recombinant or of synthetic origin, including proteins, polypeptides, peptides, nucleic acids, organic macromolecules, synthetic organic compounds, polysaccharides and other sugars, fatty acids, and lipids, and antibodies and fragments thereof, including, but not limited to, humanized or chimeric antibodies, F(ab), F(ab)$_2$, a single-chain antibody alone or fused to other polypeptides or therapeutic or diagnostic monoclonal antibodies to cancer antigens. The active agents can fall under a variety of biological activity and classes, such as vasoactive agents, neuroactive agents, hormones, anticoagulants, immunomodulating agents, cytotoxic agents, antibiotics, antiviral agents, antigens, infectious agents, inflammatory mediators, hormones, and cell surface antigens. More particularly, active agents can include, in a non-limiting manner, cytokines, lipokines, enkephalins, alkynes, cyclosporins, anti-IL-8 antibodies, IL-8 antagonists including ABX-IL-8; prostaglandins including PG-12, LTB receptor blockers including LY29311, BIIL 284 and CP105696; triptans such as sumatriptan and palmitoleate, insulin and analogs thereof, growth hormone and analogs thereof, parathyroid hormone (PTH) and analogs thereof, parathyroid hormone related peptide (PTHrP), ghrelin, obestatin, enterostatin, granulocyte macrophage colony stimulating factor (GM-CSF), amylin, amylin analogs, glucagon-like peptide 1 (GLP-1), Texas Red, clopidogrel, PPACK (D-phenylalanyl-L-prolyl-L-arginine chloromethyl ketone), oxyntomodulin (OXM), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, nociceptin, nocistatin, orphanin FQ2, calcitonin, CGRP, angiotensin, substance P, neurokinin A, pancreatic polypeptide, neuropeptide Y, delta-sleep-inducing peptide and vasoactive intestinal peptide.

The drug content to be delivered on microparticles formed from FDKP having a trans isomer content between 45% and 65% is typically greater than 0.01%. In one embodiment, the drug content to be delivered with the microparticles having the aforementioned trans isomer content, can range from about 0.01% to about 20%, which is typical for peptides such as insulin. For example, if the drug is insulin, the present microparticles typically comprise 3-4 U/mg (approximately 10 to 15%) insulin. In certain embodiments, the drug content of the particles can vary depending on the form and size of the drug to be delivered.

Manufacture of Microparticles

In one embodiment and disclosed herein is a manufacturing process that can be used to produce FDKP microparticles comprising a trans isomer content of from about 45% to about 65% and insulin.

Figure 5:
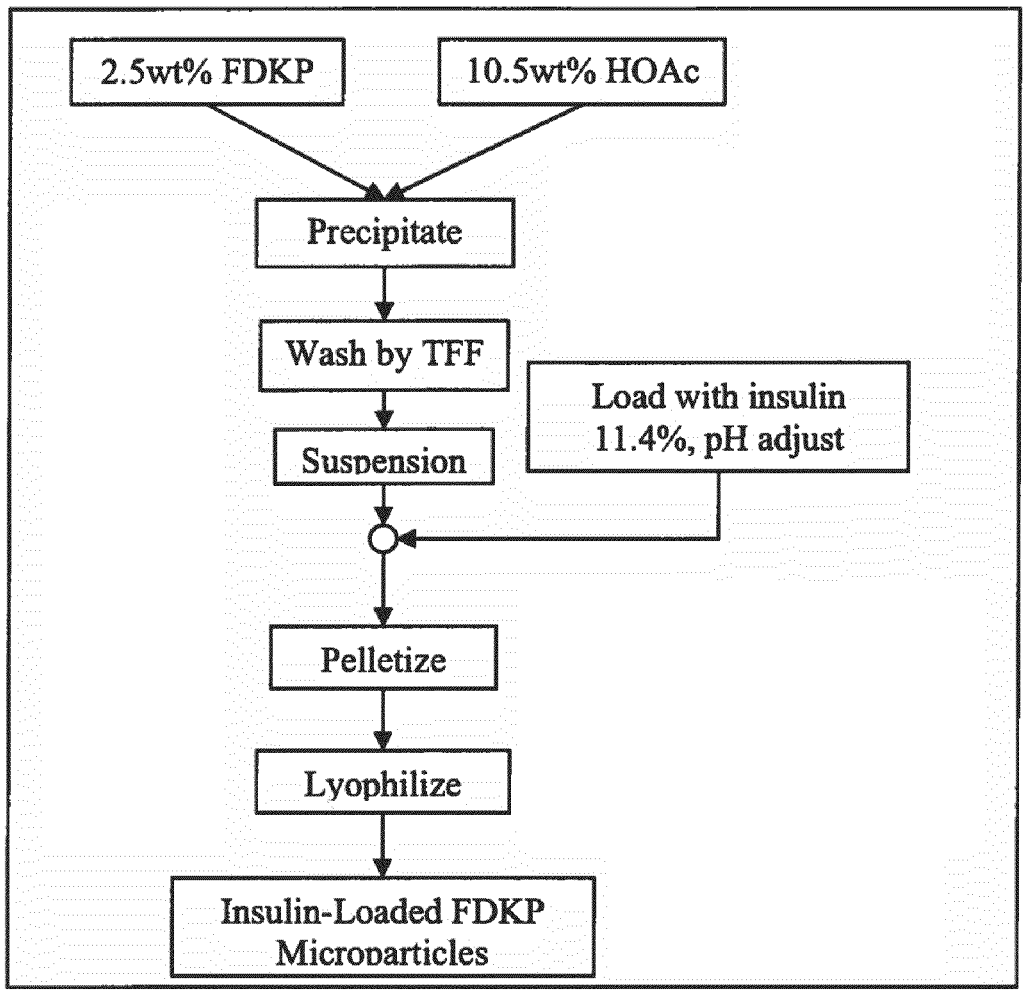
FIG. 5 depicts a schematic of a process to manufacture insulin-loaded FDKP microparticles with a trans isomer content of about 45% to about 65%.

FIG. 5 depicts a schematic representation of a manufacturing process for making the present FDKP microparticles containing insulin. In summary, using a dual-feed high shear mixer, for example, as disclosed in U.S. Provisional Patent Application Ser. No. 61/257,311, filed on Nov. 2, 2009, which disclosure is incorporated herein by reference in its entirety, equal masses of about 10.5 wt % acetic acid and about 2.5 wt % FDKP solutions at about 16° C.±about 2° C. (Table 2 and 3) can be fed at 2000 psi through a 0.001-in$^2$ orifice. The precipitate can be collected in a deionized (DI) water reservoir of about equal mass and temperature. The resultant suspension contains about 0.8% solids. The precipitate can be concentrated and washed by tangential flow filtration. The precipitate can be first concentrated to about 4% solids then washed with deionized water. The suspension can be finally concentrated to about 10% solids based on the initial mass of FDKP. The concentrated suspension can be assayed for solids content by an oven drying method.

A concentrated insulin stock solution can be prepared with 1 part insulin and 9 parts about 2% wt acetic acid. The insulin stock can be added gravimetrically to the suspension to obtain a load of about 11.4% wt. The insulin-containing suspension can be mixed at least about 15 minutes, and then titrated with about 14 to about 15 wt % aqueous ammonia to a pH of about 4.5 from an initial pH of about 3.5. The suspension can be flash-frozen in liquid nitrogen to form pellets using a cryogranulator, for example, as disclosed in U.S. Provisional Patent Application Ser. No. 61/257,385, filed on Nov. 2, 2009, which disclosure is incorporated herein by reference in its entirety, and lyophilized to yield the bulk insulin-loaded FDKP microparticles with a % trans isomer content of between about 45% and 65%. Blank FDKP microparticles can be manufactured identically minus the insulin loading and pH adjustment steps.

TABLE 2

10.5% Acetic Acid Solution

| Component | wt % |
|---|---|
| DI Water | 89.00 |
| GAA | 10.50 |
| 10% Polysorbate 80 | 0.50 |

0.2 μm filtered

TABLE 3

2.5% FDKP Solution

| Component | wt % |
|---|---|
| DI Water | 95.40 |
| FDKP | 2.50 |
| NH$_4$OH | 1.60 |
| 10% Polysorbate 80 | 0.50 |

0.2 μm filtered

As used herein, "solvent" refers to the fluid medium in which the active agent and microparticle are "bathed." It should not be interpreted to require that all components are in solution. Indeed in many instances it may be used to refer to the liquid medium in which the microparticles are suspended.

As is evident from the foregoing disclosure, microparticles of embodiments disclosed herein can take many different forms and incorporate many different drugs or active agents. The common attribute of each of these embodiments, however, is that the formed microparticles have a trans isomer content of about 45% to about 65%.

EXAMPLES

The following examples are included to demonstrate embodiments of the disclosed microparticles. It should be appreciated by those of skill in the art that the techniques disclosed in the examples which follow represent techniques discovered by the inventor to function well in the practice of the present disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the scope of the invention.

Example 1

I. Relationship Between Trans Isomer Content and RF/Fill

Microparticles were manufactured from FDKP and insulin. FDKP was dissolved in aqueous NH$_4$OH to form a solution. A feed stream of this solution was combined with a feed stream of an aqueous HOAc solution in a high shear mixer to form an aqueous suspension of microparticles.

The FDKP feed solution was prepared with about 2.5 wt % FDKP, about 1.6 wt % concentrated NH$_4$OH (about 28 to about 30 wt % NH$_3$) and about 0.05 wt % polysorbate 80. The acetic acid feed solution was prepared at about 10.5 wt % GAA and about 0.05 wt % polysorbate 80. Both feed solutions were filtered through an about 0.2 µm membrane prior to use.

Equal amounts (by mass) of each feed solution were pumped through a DUAL-FEED SONOLATOR™ equipped with the #5 orifice (0.0011 sq. inch). The minor pump was set to 50% for equal flow rates of each feed stream and the feed pressure was about 2000 psi. The receiving vessel contained deionized (DI) water equal to the mass of either feed solution (e.g. 4 kg FDKP feed solution and 4 kg HOAc feed solution would be pumped through the SONOLATOR™ into the receiving vessel containing 4 kg of DI water).

The resulting suspension was concentrated and washed by means of tangential flow filtration using a 0.2 m$^2$ PES membrane. The suspensions were first concentrated to about 4% solids then diafiltered with DI water and finally concentrated to about 16% nominal solids. The actual percent solids of the washed suspension was determined by "loss on drying."

Insulin stock solutions were prepared containing about 10 wt % insulin (as received) in a solvent comprising about 2 wt % HOAc in DI water and sterile filtered. The stock solution was filtered through a 0.22 µm filter prior to use. Based on the solids content of the suspension, the appropriate amount of stock solution was added to the mixed suspension. The resulting microparticle/insulin mixture was then adjusted from a pH of about 3.6 to a pH of about 4.5 using an ammonium hydroxide solution.

The microparticle/insulin suspension was then pelletized (cryo-granulated) by flash freezing by in liquid nitrogen. The ice pellets were lyophilized to produce a dry powder.

The respirable fraction on fill (RF/fill) of bulk powders is a measure of aerodynamic microparticle size distribution and is determined by testing with the Andersen cascade impactor. To obtain RF/fill values, cartridges are filled with bulk powder and discharged through a MEDTONE® inhaler at 30 L/min. The powder collected on each inhaler stage is weighed and the total powder collected is normalized to the total amount filled in the cartridges. Accordingly, RF/fill is powder collected on those stages of the impactor representing the respirable fraction divided by powder loaded into cartridges.

As shown in FIG. 1, FDKP powders with acceptable aerodynamic performance measured as RF/fill have been produced from FDKP with as little as 45% trans isomer content (FIG. 1). Powders containing more than 65% trans-FDKP tended to have lower and more variable RF/fill.

The studies determined the trans isomer content range with beneficial aerodynamic properties. The next sections describe experiments conducted to evaluate processing conditions that can generate the specified isomer contents.

II. Saponification Solvent

Experiments were conducted to determine the effect, if any, of the saponification conditions on FDKP trans isomer content (FIG. 2). A mixture of FDKP diethyl ester (Compound 004) and 590 mL of reaction solvent (see Table 5) was heated to about 57° C. After the reaction temperature had stabilized, about 50% NaOH solution was added dropwise via addition funnel over about 60 minutes. The reaction was held for about 30 minutes after the NaOH addition was complete and then filtered to remove any unreacted solids. The filtrate was acidified with acetic acid to a pH of about 5 and the resulting solids isolated by filtration, washed with water and acetone, dried in a vacuum oven, and analyzed by HPLC to determine cis and trans isomer content.

Accordingly, five different solvent systems ranging from aqueous (Table 4, A) to organic (Table 4, E) were evaluated. In general, the data in Table 4 show that the solvent system used in experiments A, B and C yielded FDKP with acceptable trans isomer content.

TABLE 4

Affect of water:methanol Solvent Ratio in Step 5 on FDKP Isomer Content

| Sample ID | Water:Methanol Ratio (v:v) | % Trans FDKP |
|---|---|---|
| A | 4:0 | 51 |
| B | 3:1 | 53 |
| C | 2:2 | 55 |
| D | 1:3 | 78 |
| E | 0:4 | 33 |

III. Recrystallization Conditions

FDKP can be recrystallized from a TFA (solvent)/GAA (anti-solvent) mixture (FIG. 2; step 6). Controlled process parameters were evaluated to characterize this recrystallization process and its effects on FDKP isomer contents. In general, recrystallization reactions with high yield also gave FDKP with a desired trans isomer content. Low yielding recrystallization reactions resulted in elevated trans isomer content, because the cis isomer has greater solubility in the recrystallization solvent system.

A reactor was charged with crude FDKP (about 75 g) and TFA (about 250 mL) and stirring was initiated. The suspension was heated to reflux (about 80° C. to about 85° C.) and held for about 10 minutes or until all solids were dissolved. The mixture was cooled to below about 60° C. Glacial acetic acid (about 375 mL) was added to the solution. The mixture was cooled and held for a minimum of about 6 hours at about 10° C. to about 20° C. The precipitated product was filtered and washed with GAA (3× about 100 mL), acetone (3× about 100 mL) and water (1× about 100 mL). The product was dried at about 55° C. under vacuum (about 22 to about 25 in. Hg) for about 12 to about 18 hours.

Initially, four factors were tested including solvent quantity, anti-solvent quantity, crystallization time and crystallization temperature. A solvent quantity of about 2.68 or about 3.34 mL/g FDKP provided acceptable % trans isomer of FDKP. At around 6.68 mL solvent/g FDKP, an unacceptably high trans isomer content was produced. The amount of anti-solvent did not significantly affect % trans FDKP isomer content at up to 5.0 mL/g FDKP. Reducing anti-solvent quantity from the control quantity substantially produced a % trans FDKP above the desired range.

In experiments with high product yield, crystallization time did not significantly affect % trans FDKP isomer content at up to about 6 or 24 hours. Isomer content (% trans isomer of FDKP) fell outside the about 45 to about 65% range at the high (35° C.) and low (0° C.) crystallization temperatures tested.

Figure 6:
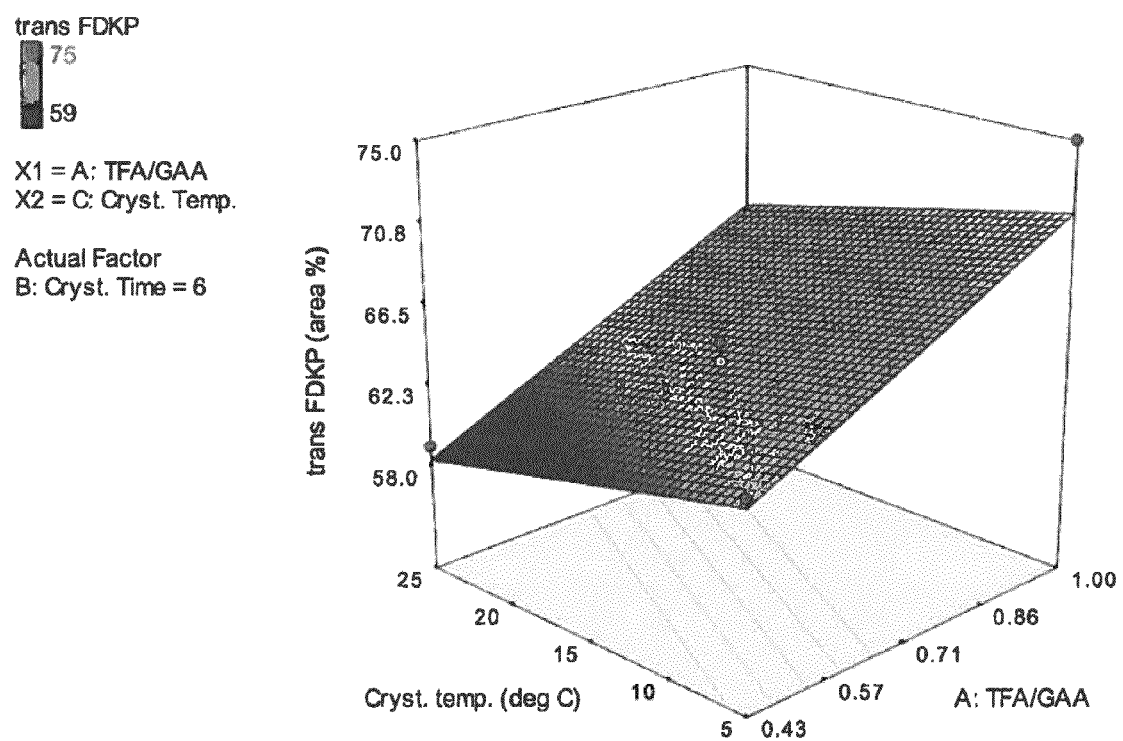
FIG. 6 depicts a response surface methodology analysis for trans isomer content.

Subsequent experiments supported these findings. FIG. 6 shows a surface depicting FDKP isomer content, measured as % trans FDKP, as a function of solvent:anti-solvent ratio (TFA:GAA) and crystallization temperature. Over the ranges tested in these experiments the values for % trans FDKP varied from 59-75%. The data suggest that trans FDKP isomer is within the desired range at a low solvent ratio (0.43) and high crystallization temperatures (25° C.). Predicted values for % trans FDKP isomer in this area of the response surface are 58-60%. These observations suggest that using a crystallization temperature of 25° C. could be advantageous.

Example 2

Measuring the Trans Isomer of FDKP

FDKP cis/trans isomer ratio was determined using HPLC. An FDKP sample was prepared at a concentration of ~0.15 mg/mL in 0.1 M ammonium formate buffer. The sample was sonicated and transferred to an HPLC vial for analysis. The injection volume used was 20 µL. Retention times of 31.7 and 33.3 minutes (cis and trans FDKP, respectively) were observed using the following HPLC parameters:
Column: Phenomenex LUNA Phenyl-Hexyl
Particle Size: 3 mm
Column Length: 15 cm
Column Internal Diameter: 3.0 mm
Mobile Phase A: water/trifluoroacetic acid, 1000:1 (v:v)
Mobile Phase B: methanol/tetrahydrofuran/trifluoroacetic acid, 900:100:1 (v:v:v)
Injection Volume: 20 µL
Flow Rate: 0.3 mL per minute
Run Time: 90 min.
Column Temperature: 30±3° C.
Sample Temperature: 8±3° C.
Detector: UV 254 nm

TABLE 5

Elution gradient of FDKP sample:

| Time (min) | % A | % B | Flow Rate (mL/min) | Comments |
|---|---|---|---|---|
| 0 | 95 | 5 | 0.3 | starting conditions |
| 75 | 53.5 | 46.5 | 0.3 | linear gradient |
| 76 | 20 | 80 | 0.3 | isocratic hold |
| 77 | 95 | 5 | 0.3 | Return to initial |
| 90 | 95 | 5 | 0.3 | Re-equilibrate |

Example 3

Geometric Particle Size Analysis of Emitted Formulations by Volumetric Median Geometric Diameter (VMGD) Characterization Laser diffraction of dry powder formulations emitted from dry powder inhalers is a common methodology employed to characterize the level of de-agglomeration subjected to a powder. The methodology indicates a measure of geometric size rather than aerodynamic size as occurring in industry standard impaction methodologies. Typically, the geometric size of the emitted powder includes a volumetric distribution characterized by the median particle size, VMGD. Importantly, geometric sizes of the emitted particles are discerned with heightened resolution as compared to the aerodynamic sizes provided by impaction methods. Smaller sizes are preferred and result in greater likelihood of individual particles being delivered to the pulmonary tract. Thus, differences in inhaler de-agglomeration and ultimate performance can be easier to resolve with diffraction. In these experiments, inhalers were tested with laser diffraction at pressures analogous to actual patient inspiratory capacities to determine the effectiveness of the inhalation system to de-agglomerate powder formulations. Specifically, the formulations included cohesive diketopiperazine powders with an active insulin loaded ingredient and without. These powder formulations possessed characteristic surface areas, isomer ratios, and Carr's indices. Reported in Table 6 are a VMGD and an efficiency of the container emptying during the testing. FDKP powders have an approximate Carr's index of 50 and TI powder has an approximate Carr's index of 40.

TABLE 6

| Inhaler system | powder | % trans | SSA | pressure drop (kPa) | sample size | % CE | VMGD (micron) |
|---|---|---|---|---|---|---|---|
| DPI 2 | FDKP | 56 | 55 | 4 | 15 | 92.5 | 6.800 |
| MedTone ® | FDKP | 56 | 55 | 4 | 30 | 89.5 | 21.200 |
| DPI 2 | FDKP + active | 56 | 45 | 4 | 30 | 98.0 | 4.020 |
| DPI 2 | FDKP + active | 56 | 45 | 4 | 20 | 97.0 | 3.700 |
| DPI 2 | FDKP + active | 56 | 45 | 4 | 20 | 98.4 | 3.935 |

TABLE 6-continued

| Inhaler system | powder | % trans | SSA | pressure drop (kPa) | sample size | % CE | VMGD (micron) |
|---|---|---|---|---|---|---|---|
| DPI 2 | FDKP + active | 56 | 45 | 4 | 20 | 97.8 | 4.400 |
| MedTone ® | FDKP + active | 56 | 45 | 4 | 10 | 86.1 | 9.280 |
| MedTone ® | FDKP + active | 56 | 45 | 4 | 10 | 92.3 | 10.676 |
| DPI 2 | FDKP + active | 56 | 45 | 2 | 7 | 92.9 | 4.364 |
| DPI 2 | FDKP + active | 56 | 45 | 2 | 7 | 95.1 | 4.680 |
| DPI 2 | FDKP + active | 56 | 45 | 4 | 7 | 97.0 | 3.973 |
| DPI 2 | FDKP + active | 56 | 45 | 4 | 7 | 95.5 | 4.250 |
| DPI 2 | FDKP + active | 56 | 56 | 4 | 10 | 99.6 | 6.254 |
| DPI 2 | FDKP + active | 56 | 14 | 4 | 10 | 85.5 | 4.037 |
| MedTone ® | FDKP + active | 56 | 56 | 4 | 20 | 89.7 | 12.045 |
| MedTone ® | FDKP + active | 56 | 14 | 4 | 20 | 37.9 | 10.776 |
| DPI 2 | FDKP + active | 54 | 50 | 4 | 10 | 97.1 | 4.417 |
| DPI 2 | FDKP + active | 54 | 44 | 4 | 10 | 96.0 | 4.189 |
| DPI 2 | FDKP + active | 56 | 35 | 4 | 10 | 92.0 | 3.235 |
| DPI 2 | FDKP + active | 50 | 34 | 4 | 10 | 93.2 | 5.611 |
| DPI 2 | FDKP + active | 66 | 33 | 4 | 10 | 79.0 | 4.678 |
| DPI 2 | FDKP + active | 45 | 42 | 4 | 10 | 93.2 | 5.610 |
| DPI 2 | FDKP + active | 56 | 9 | 4 | 10 | 78.9 | 5.860 |

The data in Table 6 show an improvement in powder de-agglomeration in inhalers identified as DPI 2 over the MEDTONE® inhaler system. Diketopiperazine formulations with surface areas ranging from 14-56 m²/g demonstrated emptying efficiencies in excess of 85% and VMGD less than 7 microns. Similarly, formulations possessing an isomer ratio ranging from 45-66% trans demonstrated improved performance over the predicate device. However, it is worth noting that even with the more efficient inhaler at 66% trans content there has been a reduction in cartridge emptying indicating a fall off (decrease) in aerodynamic performance as trans isomer content departs from the ranges disclosed herein. Lastly, performance of the inhaler system with formulations characterized with Carr's indices of 40-50 were shown to be improved over the predicate device as well. In all cases, the reported VMGD values were below 7 microns.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A fumaryl diketopiperazine (FDKP) composition comprising a trans isomer content of about 45% to about 65%.

2. The FDKP composition according to claim 1, wherein said trans isomer content is from about 50% to about 65%.

3. The FDKP composition according to claim 1, wherein said trans isomer content is from about 53% to about 63%.

4. Fumaryl diketopiperazine (FDKP) microparticles comprising the FDKP composition of claim 1.

5. FDKP microparticles according to claim 4, wherein said trans isomer content is from about 50% to about 65%.

6. FDKP microparticles according to claim 4, wherein said trans isomer content is from about 53% to about 63%.

7. FDKP microparticles according to claim 4, further comprising a drug or an active agent.

8. FDKP microparticles according to claim 7, wherein said drug or active agent is a peptide or protein.

9. FDKP microparticles according to claim 8, wherein said peptide is an endocrine hormone.

10. FDKP microparticles according to claim 9, wherein said endocrine hormone is insulin, parathyroid hormone, calcitonin, glucagon, glucagon-like peptide 1, oxyntomodulin, an analog or active fragment of said endocrine hormone.

11. The microparticles of claim 4, wherein the drug is present in an amount greater than 0.01 wt % of the microparticles.

12. A dry powder comprising the microparticles of claim 4.

13. A dry powder comprising the microparticles of claim 7.

14. A method of treating an endocrine-related disease or disorder comprising administering to a person in need thereof a dry powder formulation comprising fumaryl diketopiperazine (FDKP) microparticles comprising an FDKP trans isomer content of about 45% to about 65% and an endocrine hormone suitable to treat said disease or disorder.

15. The method of claim 14, wherein the endocrine hormone is insulin, parathyroid hormone, calcitonin, glucagon, glucagon-like peptide 1, oxyntomodulin, or an analog of said endocrine hormone.

16. The method of claim 14, wherein the endocrine-related disease is diabetes.

17. A method of making microparticles suitable for pulmonary administration as a dry powder comprising:
    a) synthesizing an FDKP compound having an FDKP trans isomer content of about 45% to about 65%;
    b) dissolving the FDKP compound in a solution having a basic pH to form an FDKP solution;
    c) providing a solution of a volatile acid, and
    d) mixing the solutions together in a high-shear mixer to produce said microparticles in a suspension.

18. The method of claim 17, further comprising determining the trans isomer content of the FDKP.

19. The method of claim 18, wherein the step of determining the trans isomer content of the FDKP is performed using high pressure liquid chromatography.

20. The method of claim 17, further comprising mixing said microparticles with a solution comprising a drug.

21. The method of claim 17, wherein the drug is an endocrine hormone.

22. The method of claim 21, wherein the drug is insulin, parathyroid hormone, calcitonin, glucagon, glucagon-like peptide 1, oxyntomodulin, or an analog of said drug.

23. A method for synthesizing a diketopiperazine having a trans isomer content of about 45% to about 65% comprising:
    a) saponifying an ester of a diketopiperazine in a mixture of water and a water-miscible solvent at a basic pH; and
    b) recrystallizing the diketopiperazine in a reaction mixture comprising trifluoroacetic acid and glacial acid at a resultant ratio ranging from about 0.4 to about 0.7.

24. The method of claim 23, wherein the water-miscible solvent is an alcohol, tetrahydrofuran, dioxane, and acetonitrile.

25. The method of claim 24, wherein the alcohol is methanol, ethanol, or isopropanol.

26. The method of claim 25, wherein the methanol is in a water:methanol ratio ranging from 1:1 to about 3:1.

27. The method of claim 23, further comprising the step of determining the trans isomer content of the diketopiperazine.

28. The method of claim 23, wherein the diketopiperazine is of the formula 2,5-diketo-3,6-bis(N—X-4-aminobutyl)piperazine, wherein X is selected from the group consisting of fumaryl, succinyl, maleyl, and glutaryl.

29. The method of claim 23, wherein the diketopiperazine is 2,5-diketo-3,6-bis(N-fumaryl-4-aminobutyl)piperazine.

30. The method of claim 23, wherein the reaction mixture in the recrystallizing step is held for a period of about 4 hours or greater than 4 hours.

* * * * *

(12) EX PARTE REEXAMINATION CERTIFICATE (53rd)
Ex Parte Reexamination Ordered under 35 U.S.C. 257

United States Patent
Kraft et al.

(10) Number: US 8,227,409 C1
(45) Certificate Issued: Apr. 20, 2016

(54) DIKETOPIPERAZINE MICROPARTICLES WITH DEFINED ISOMER CONTENTS

(75) Inventors: Kelly S. Kraft, Poughquag, NY (US); Karla Somerville, Corona, CA (US)

(73) Assignee: MANNKIND CORPORATION, Valencia, CA (US)

Supplemental Examination Request:
No. 96/000,027, Aug. 30, 2013

Reexamination Certificate for:
Patent No.: 8,227,409
Issued: Jul. 24, 2012
Appl. No.: 12/813,839
Filed: Jun. 11, 2010

Related U.S. Application Data

(60) Provisional application No. 61/186,779, filed on Jun. 12, 2009.

(51) Int. Cl.

| | | |
|---|---|---|
| *A61K 47/22* | (2006.01) | |
| *A61K 38/22* | (2006.01) | |
| *A61K 38/28* | (2006.01) | |
| *A61K 38/29* | (2006.01) | |
| *A61K 38/02* | (2006.01) | |
| *A61K 38/26* | (2006.01) | |
| *A61P 3/10* | (2006.01) | |
| *C07D 241/08* | (2006.01) | |
| *A61K 38/23* | (2006.01) | |
| *A61K 9/16* | (2006.01) | |
| *A61K 9/00* | (2006.01) | |

(52) U.S. Cl.
CPC ............... *A61K 9/1635* (2013.01); *A61K 38/28* (2013.01); *A61K 9/0073* (2013.01); *A61K 2300/00* (2013.01)

(58) Field of Classification Search
None
See application file for complete search history.

(56) References Cited

To view the complete listing of prior art documents cited during the supplemental examination proceeding and the resulting reexamination proceeding for Control Number 96/000,027, please refer to the USPTO's public Patent Application Information Retrieval (PAIR) system under the Display References tab.

*Primary Examiner* — Evelyn Huang

(57) ABSTRACT

Disclosed herein are fumaryl diketopiperazine (FDKP) compositions and microparticles having a specific trans isomer content of about 45% to about 65%. The FDKP microparticles can comprise a drug such as an endocrine hormone, including, peptide, including, insulin, glucagon, parathyroid hormones and the like and can be used to make a powder formulation for pulmonary delivery of the drug.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

The patentability of claims 23-30 is confirmed.

Claims 1-22 are cancelled.

\* \* \* \* \*